United States Patent [19]

McAndrews

[11] 4,384,851

[45] May 24, 1983

[54] BUTTERFLY CFC ARCH BRACE

[76] Inventor: James R. McAndrews, 3233 Sherwood Forest Blvd., Baton Rouge, La. 70816

[21] Appl. No.: 316,114

[22] Filed: Oct. 29, 1981

Related U.S. Application Data

[63] Continuation-in-part of Ser. No. 264,036, May 15, 1981.

[51] Int. Cl.³ .............................................. A61C 7/00
[52] U.S. Cl. ......................................................... 433/7
[58] Field of Search ............................................. 433/7

[56] References Cited

U.S. PATENT DOCUMENTS 2,262,108  11/1941  Linde ........................................ 433/7

Primary Examiner—Robert Peshock
Attorney, Agent, or Firm—Roy, Kiesel, Patterson & McKay

[57] ABSTRACT

A continuous force control (CFC) brace for expansion of the lower oral arch is disclosed comprising a first wire attached at each end to opposite molar teeth and positioned to prevent movement of pre-determined teeth and a second wire attached to the middle section of the first wire and extending outward from both sides thereof, the second wire being constructed from smaller diameter wire than the first wire and positioned to apply a small continuous force against those teeth which are desired to be repositioned.

3 Claims, 3 Drawing Figures

BUTTERFLY CFC ARCH BRACE

RELATED APPLICATIONS

This is a continuation-in-part of the U.S. patent application Ser. No. 264,036 filed May 15, 1981 by the inventor herein and entitled CFC Expansion Arch, mention of which is made for purposes of obtaining benefit of its earlier filing date.

BACKGROUND OF THE INVENTION

1. Field of the Invention

This invention relates in general to orthodonic devices and more particularly to continuous force control orthodonic devices.

2. Prior Art

A great deal of research time and money has been spent to develop devices for straightening teeth. Examples of representative art are seen in the disclosures found in the following patents:

| U.S. PAT. NO. | ISSUED | TITLE |
| --- | --- | --- |
| U.S. McCarter Pat. No. 1,395,922 | 11/1/21 | Dental Expansion Arch |
| U.S. Fernald Pat. No. 1,471,785 | 10/23/23 | Orthodontic Appliance |
| U.S. Craigs Pat. No. 1,764,067 | 6/17/30 | Orthodontic Appliance |
| U.S. Eaton Pat. No. 1,481,861 | 1/29/24 | Orthodontic Appliance |
| U.S. Kesling Pat. No. 3,055,110 | 9/25/62 | Buccal Attachment |
| U.S. Rubin Pat. No. 3,477,129 | 11/11/69 | Orthodontic Appliance |

Even those designs which utilize the continuous force control method such as discussed in the article published in "Biomechanics of the Light Progressive Technique (No. 7)" entitled "Mandibular Utility Arch" by Robert M. Ricketts et al., a copy of which can be found in the file history of applicant's U.S. Pat. No. 4,192,069 issued Mar. 11, 1980 and entitled "Utility Arch", still require constant adjustment as the teeth begin their movement. This requires the patient to make many trips back to the dentist office and can result in the incorrect pressure being applied to the teeth if the subsequent trips are delayed or not made.

SUMMARY OF THE INVENTION

Therefore, it is an object of this invention to provide a single arch device which, when positioned in the mouth, will provide a constant light continuous force against those teeth to be moved even after they have started their movement.

Another object of this invention is to provide an arch device that maintains correctly positioned teeth situated while other pre-determined teeth are being moved by the same device.

Still another object of this invention is to provide an arch device which selectively moves certain teeth by unobtrusive positioning behind the teeth.

Other objects and advantages of this invention will become apparent from the ensuing descriptions of the invention.

Accordingly, an orthodonic brace is provided comprising a first wire that is attachable at its opposite ends to the molar by anchoring rings or band and shaped to fixedly contact those correctly positioned teeth to maintain them in a stationary position, and a second wire attached to the middle section of the first wire and extending outward from both sides thereof, the second wire being adjustable arcuately shaped to contact those teeth incorrectly positioned, the second wire being constructed from a smaller diameter wire than the first wire, and preferably located beneath the first wire.

PREFERRED EMBODIMENTS OF THE INVENTION

Figure 1:
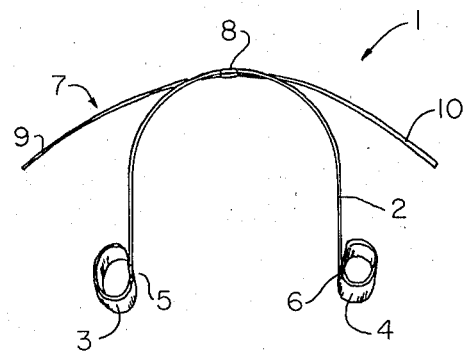
FIG. 1 is a three-dimensional view of a preferred embodiment of the invention.

Referring now to FIG. 1, a preferred embodiment of the orthodonic device 1 used for mandibular arch development is shown comprising a first wire 2 having conventional anchoring rings or bands 3 and 4 attached at opposite ends 5 and 6, respectively, of wire 2. A second wire 7 is attached by soldering or other method to the mid-section 8 of wire 2. Second wire 7 extends outward in arcuate fashion preferably below and beyond wire 2 as shown.

In this embodiment, wire arms 9 and 10 will exert an outward force when forced inward toward wire 2. By designing the degree of arcuate curve, the amount of outward force exerted against the teeth, as described below, can be pre-set.

Figure 2:
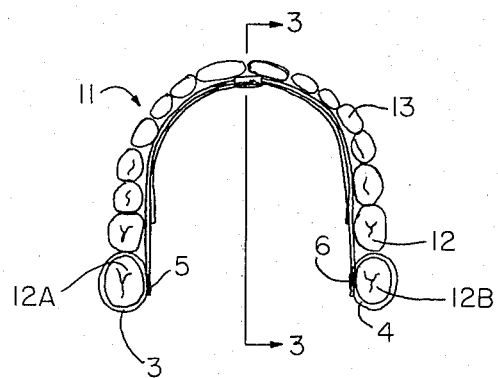
FIG. 2 is a three-dimensional top view of a preferred embodiment of the butterfly CFC brace positioned in the lower arch.
Figure 3:
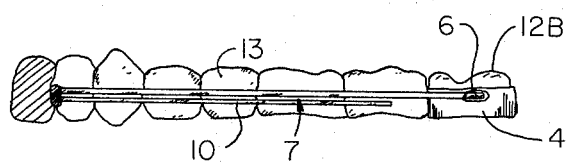
FIG. 3 is a partial three-dimensional side view of FIG. 2 taken along lines 2—2.

Turning now to FIGS. 2 and 3, orthodonic device 1 is placed inside the mandibular arch 11 consisting of teeth 12 which are correctly positioned and teeth 13 which are incorrectly positioned. Device 1 is anchored in place by bands 3 and 4 being fitted about molar teeth 12A and 12B, respectively. Wire 2 is then bent to be fixedly positioned against teeth 12 to prevent their movement during the time wire 7 is acting against teeth 13. For this purpose it is preferred that wire 2 have a diameter of at least 0.032–0.040 inches and most preferably about 0.036 inches.

Wire arms 9 and 10 are then bent and cut so that they apply the desired amount of continuous force against teeth 13. The amount of force will depend upon, by way of example only, which teeth are being effected, the degree and type of movement desired, the size and age of the teeth, and the physical relationship of the other mandibular teeth to one another.

In a preferred embodiment, wire 7 will have a diameter no greater than 0.014–0.020 inches, and most preferably 0.016 inches. This feature allows great flexibility in the positioning of wire arms 9 and 10 and insures that the desired continuous light force can be achieved. Thus, as tooth 13 is gradually moved into the desired position, wire arm 10 will continually push against tooth 13 due to the outward spring force achieved by the initial inward compression of arm 10 from its original position.

It is also preferred that wire 7 be attached and positioned below wire 2 in order to reduce or eliminate the possibility that wire 7 would pop out of position and cause damage or injury to the tongue or mouth.

There are, of course, many alternate embodiments of this invention not specifically mentioned, but which are intended to be included within the scope of this invention as defined by the following claims.

What I claim is:

1. An orthodonic brace for adjusting the position of teeth in the lower arch which comprises:
 (a) a first wire attachable at its opposite ends to opposite molar teeth, respectively, said wire being adjustably shaped to fixedly contact pre-determined teeth which are not desired to be moved; and
 (b) a second wire attached at its mid-section to the mid-section of said first wire and extending out therefrom and adjustable in a convex arcuate fashion to contact other teeth in said arch and being constructed of sufficiently small diameter to apply a continuous light force against said other teeth during the period of time that said brace is positioned in said lower arch.

2. An orthodonic brace according to claim 1 wherein said second wire is constructed from a smaller diameter wire than said first wire.

3. An orthodonic brace according to claim 1 wherein said first wire has a diameter of at least 0.032–0.040 inches and said second wire has a diameter of less than 0.014–0.020 inches.

* * * * *